(12) United States Patent
Shilton et al.

(10) Patent No.: US 11,318,326 B2
(45) Date of Patent: May 3, 2022

(54) STRONTIUM SEALED SOURCE

(71) Applicant: QSA GLOBAL, INC., Burlington, MA (US)

(72) Inventors: Mark G. Shilton, Chelmsford, MA (US); Mark W. Vose, Windham, NH (US); Jason W. Bourn, Stratham, NH (US)

(73) Assignee: QSA GLOBAL INC., Burlington, MA (US)

( * ) Notice: Subject to any disclaimer, the term of this patent is extended or adjusted under 35 U.S.C. 154(b) by 316 days.

(21) Appl. No.: 16/513,032

(22) Filed: Jul. 16, 2019

(65) Prior Publication Data

US 2019/0336791 A1 Nov. 7, 2019

Related U.S. Application Data

(63) Continuation-in-part of application No. 15/571,310, filed as application No. PCT/US2016/022437 on Mar. 15, 2016, now Pat. No. 10,714,226.

(60) Provisional application No. 62/158,091, filed on May 7, 2015.

(51) Int. Cl.
| | | |
|---|---|---|
| *A61N 5/10* | (2006.01) | |
| *A61K 51/12* | (2006.01) | |
| *G21G 4/08* | (2006.01) | |
| *A61F 9/00* | (2006.01) | |
| *A61K 51/02* | (2006.01) | |

(52) U.S. Cl.
CPC .......... *A61N 5/1017* (2013.01); *A61K 51/025* (2013.01); *A61K 51/1282* (2013.01); *G21G 4/08* (2013.01); *A61F 9/0017* (2013.01); *A61N 2005/1024* (2013.01); *A61N 2005/1089* (2013.01); *A61N 2005/1094* (2013.01)

(58) Field of Classification Search
CPC ...... A61N 5/1017; A61N 5/1001–1029; A61K 51/1282; A61K 51/00–1296; A61K 2121/00; A61K 2123/00; G21G 4/00–10
See application file for complete search history.

(56) References Cited

U.S. PATENT DOCUMENTS

| | | | |
|---|---|---|---|
| 2,517,568 A | 8/1950 | Hissong | |
| 4,284,887 A | 8/1981 | Kusumoto et al. | |
| 6,030,333 A * | 2/2000 | Sioshansi | A61N 5/1007 600/3 |
| 6,443,881 B1 | 9/2002 | Finger | |
| 6,907,106 B1 | 6/2005 | McIntyre et al. | |

(Continued)

FOREIGN PATENT DOCUMENTS

| | | |
|---|---|---|
| CN | 101951965 | 1/2001 |
| CN | 1413748 | 4/2003 |

(Continued)

OTHER PUBLICATIONS

International Search Report issued in PCT/US2020/039845 dated Feb. 3, 2021.

*Primary Examiner* — Thaddeus B Cox
(74) *Attorney, Agent, or Firm* — McCarter & English LLP

(57) ABSTRACT

The disclosure pertains to a strontium-90 sealed radiological or radioactive source, such as may be used with treatment of the eye or other medical or industrial processes. The sealed radiological source includes a radiological insert within an encapsulation. The encapsulation may include increased shielding in the center thereof.

3 Claims, 6 Drawing Sheets

(56) References Cited

U.S. PATENT DOCUMENTS

| | | | |
|---|---|---|---|
| 7,070,554 B2 | 7/2006 | White et al. | |
| 8,430,804 B2 | 4/2013 | Brigatti et al. | |
| 9,873,001 B2 | 1/2018 | Lutz et al. | |
| 2004/0242953 A1* | 12/2004 | Good | A61N 5/1027 600/7 |
| 2009/0156881 A1* | 6/2009 | Stokes | A61N 5/1017 600/7 |
| 2010/0004499 A1 | 1/2010 | Brigatti et al. | |
| 2013/0240761 A1 | 9/2013 | Wang | |
| 2015/0105601 A1* | 4/2015 | Finger | A61K 51/1251 600/1 |
| 2016/0184606 A1* | 6/2016 | Fluhs | A61N 5/1017 600/8 |
| 2016/0375267 A1 | 12/2016 | Lutz et al. | |
| 2018/0296855 A1 | 10/2018 | Lohrenz | |

FOREIGN PATENT DOCUMENTS

| | | |
|---|---|---|
| EP | 1529554 | 5/2005 |
| GB | 2350718 | 12/2000 |
| JP | 2011-508654 | 3/2011 |
| WO | 92/03179 | 3/1992 |
| WO | 2000/075692 | 12/2000 |
| WO | 01/87409 | 11/2001 |
| WO | 2015105539 | 7/2015 |
| WO | PCT/US2014/056135 | 3/2016 |
| WO | 2016/178746 | 11/2016 |

\* cited by examiner

STRONTIUM SEALED SOURCE

This application is a continuation-in-part application of U.S. patent application Ser. No. 15/571,310, filed on Nov. 2, 2017, now U.S. Pat. No. 10,714,226, which claims priority of PCT/US2016/022437, filed Mar. 15, 2016, which claims priority under 35 U.S.C. 119(e) of U.S. provisional application Ser. No. 62/158,091, filed on May 7, 2015, the contents of all of which is hereby incorporated by reference in its entirety and for all purposes.

BACKGROUND OF THE DISCLOSURE

Field of the Disclosure

The disclosure pertains to a strontium-90 scaled source, such as may be used with treatment of the eye or other medical, brachytherapeutic or industrial processes. In particular, a relatively constant absorbed dose rate is sought throughout a target volume of tissue of therapeutic interest that is to be treated with radiation (hereinafter referred to as "a flat radiation profile").

Description of the Prior Art

The prior art of radiological or radioactive sources of various types for medical, industrial and other processes is well-developed. For example, U.S. Pat. No. 8,430,804, entitled "Methods and Devices for Minimally-Invasive Extraocular Delivery of Radiation to the Posterior Portion of the Eye", issued on Apr. 30, 2013 to Brigatti et al., and assigned on its face to Salutaris Medical Devices, Inc., discloses an applicator for minimally-invasive delivery of beta radiation from a radionuclide brachytherapy source to the posterior portion of the eye. In particular, this is adapted for the treatment of various diseases of the eye, such as, but not limited to, wet age-related macular degeneration. Other prior art includes U.S. Pat. No. 9,873,001 entitled "Methods and Devices for Minimally-Invasive Delivery of Radiation to the Eye", issued on Jan. 23, 2018 to Lutz et al. and assigned on its face to Salutaris Medical Devices, Inc.; PCT/US2014/056135 entitled "Radiation System with Emanating Source Surrounding an Internal Attenuation Component", filed on Mar. 18, 2016; U.S. Pat. No. 7,070,554 entitled "Brachytherapy Devices and Methods of Using Them", issued on Jul. 4, 2006 to White et al., and assigned on its face to Theragenics Corporation and U.S. Pat. No. 6,413,881, entitled "Ophthalmic Brachytherapy Device", issued on Sep. 3, 2002 to Finger.

While this prior art is well-developed and suited for its intended purposes, further improvements are sought in the radioactive sources used in the disclosed devices. In particular, a collimated distribution of radiation, rather than an isotropic (spherical "$4\pi$") distribution of radiation, would allow a radiological source to direct radiation at the tissues under treatment, while reducing radiation directed at surrounding tissues which are not under treatment and also while preventing excessive radiation to be directed to the tissues under treatment in the center of the emitted radiation beam.

OBJECTS AND SUMMARY OF THE DISCLOSURE

It is therefore an object of the present disclosure to provide improvements in the radiological sources used in brachytherapy and in other medical or industrial applications. In particular, it is an object of the present disclosure to provide improved radiological sources for known applicators for treatment of diseases of the eye, including, but not limited to, wet age-related macular degeneration. These radiological sources are intended to concentrate the radiation more uniformly on the diseased tissue, rather than using isotropic radiation which would expose more of the surrounding healthy tissue to unnecessary radiation and could overexpose tissue under treatment at the center of the radiation beam.

This and other objects are attained by providing a beta radiological source, typically containing strontium-90, wherein the radiological insert has increased radioactivity around its periphery and less radioactivity at its center. This may be achieved by a toroidal or annular shape, (such as a donut-type shape with a hole or aperture in the middle) or with the central portion of a disk having reduced thickness or reduced radioactivity content. This may further be achieved by a minus lens meniscus shape wherein the lower concave surface has a shorter radius of curvature than the upper concave surface, thereby resulting in a raised thinner portion and a lower thicker peripheral portion. This is further achieved by providing an encapsulation with increased shielding in the center of the face from which the therapeutic radiation is emitted, thereby substantially attenuating the radiation emitted from the central portion of a source. It is further possible to use a separate denser attenuating disk in front of the activity, either on the inside or outside of the encapsulation. Material in the attenuating disk may include, but is not limited to, silver, copper, lead, tungsten, gold and/or iridium.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENTS

Figure 1:
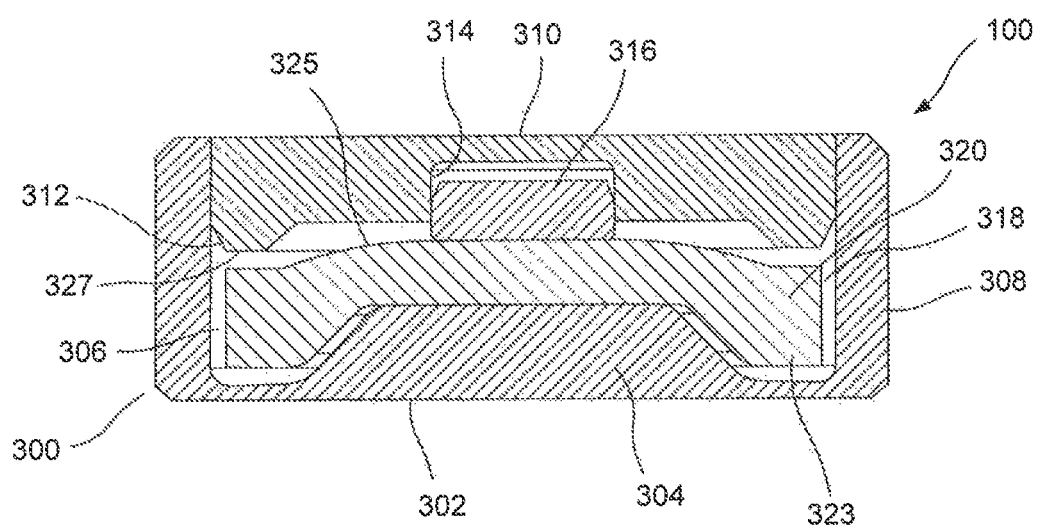
FIG. 1 is a cross-sectional view of an embodiment of a radiological source of the present disclosure.

Referring now to the drawings in detail wherein like numerals refer to like elements throughout the several views, one sees that FIG. 1 illustrates a cross-sectional view of an embodiment of the radiological source 100. The radiological source 100 is substantially rotationally symmetric, including cylindrical, annular and toroidal shapes. A capsule body 300, typically made of titanium or stainless steel, includes a lower floor 302 with a central plateau 304 thereby forming a toroidal channel 306 between the central plateau 304 (thereby increasing the beta shielding in central portions of the lower floor 302) and the outer cylindrical wall 308 of the capsule body 300. The upper edge of outer cylindrical wall 308 forms a circular opening for receiving outer lid 310 which is generally cylindrical but includes a chambered lower circular edge 312 and further includes a central cylindrical blind opening 314 for receiving telescoping inner lid 316, and typically forming a tight friction or interference fit therebetween in order to tightly position the radiological insert 318 within the capsule body 300. Outer lid 310, which is typically made of titanium or stainless steel and illustrated with an interior circumferential toroidal ridge 327, is typically welded to capsule body 300, using conventional standards of the industry. Strontium-90 radiological insert 318 (similar to insert 130 in previous embodiments) includes an upper circular or disk-shaped portion 320 which is engaged between a lower edge of telescoping inner lid 316 and central plateau 304 of capsule body 300. This configuration is intended to reduce rattling of the strontium-90 radiological insert 318. The upper surface of strontium-90 radiological insert 318 includes a convex central region 325. This convex central region 325 is intended to reinforce the structure and avoid or minimize warping and possible delamination during production. Strontium-90 radiological insert 318 further includes a downwardly extending circumferential toroidal portion 323 which extends into toroidal channel 306 of capsule body 300.

Figure 2:
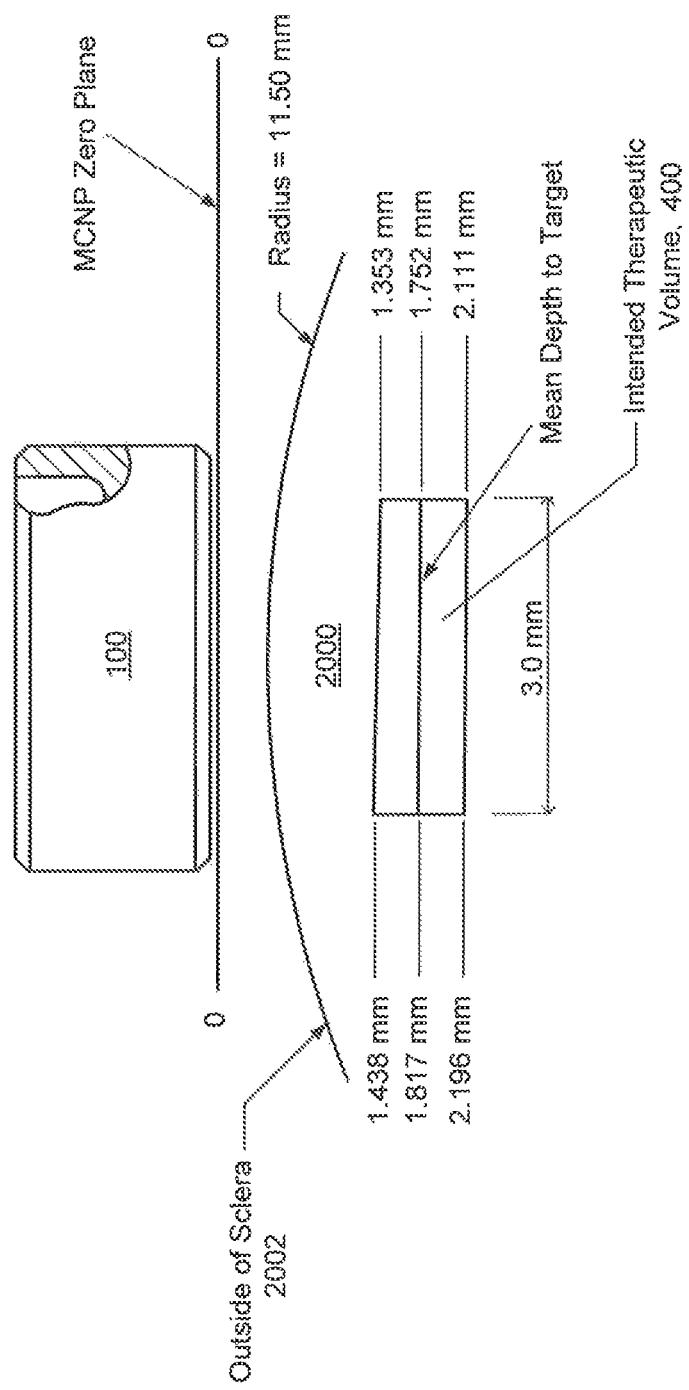
FIG. 2 is an illustration relating to the radiation dose profile generated by the radiological source of FIG. 1.
Figure 4:
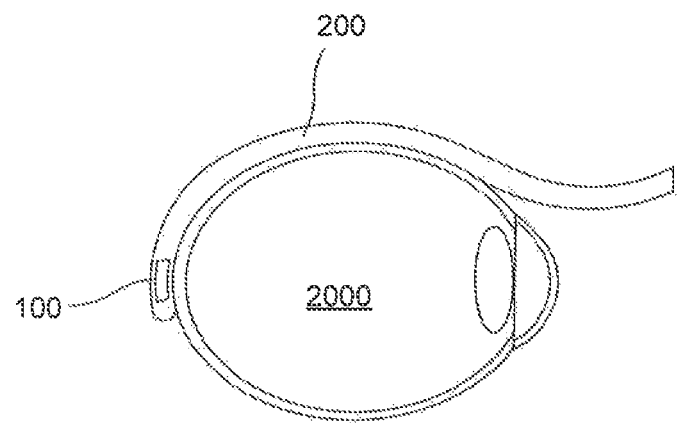
FIG. 4 illustrates a placement of the radiological source with respect to a human eyeball during medical treatment.
Figure 5:
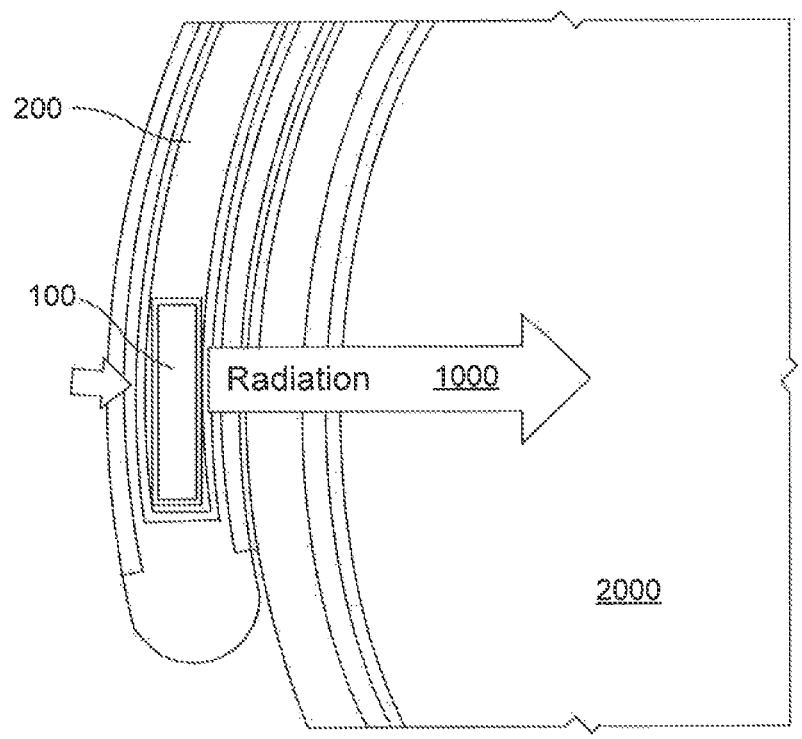
FIG. 5 illustrates a portion of FIG. 4 in greater detail.

The toroidal shape of the strontium-90 radiological insert 318, with its thickened periphery, leads to increased radiation emission around the periphery and a reduced radiation output within the center. This, in combination with the increased beta shielding in the central area of central plateau 304, results in a flat beam profile, achieving a more constant absorbed dose rate throughout a target volume of tissue of therapeutic interest that is located in front of the source as illustrated in FIG. 2, wherein typical values are given for a radiological source 100 of a diameter of 4.05 millimeters and a maximum height of 1.75 millimeters. In the given example, a intended therapeutic volume 400 with a diameter of 3.0 millimeters and a depth of 1.438 to 2.196 millimeters (with a mean depth to target of 1.817 millimeters from the lower surface of the radiological source 100) in a first case or a depth of 1.353 to 2.111 millimeters (with a mean depth to target of 1.752 millimeters from the lower surface of the radiological source 100) in a second case. A radius of 11.50 millimeters is typical for the sclera 2002 (outer covering) of a human eyeball 2000 (see also FIGS. 4 and 5). Those skilled in the art, after review or this disclosure, will understand that different structural parameters will result in different radiation distributions, as may be required by the specific application.

It is noted that the strontium-90 beta radiation insert 130 may be made of various materials, such as a strontium ceramic, strontium glass, or a collection of tightly packed ceramic beads (of various possible shapes) or a refractory-metal composite. Refractory ceramics and glasses containing Strontium-90 can be made from a wide variety of materials in combination, such as those containing metal oxides of aluminum, silicon, zirconium, titanium, magnesium, calcium amongst others. It is envisioned that other additional materials may be selected from, but not limited to, such strontium-90 compounds as $SrF_2$, $Sr_2P_2O_7$, $SrTiO_3$, $SrO$, $Sr_2TiO_4$, $SrZrO_3$, $SrCO_3$, $Sr(NbO_3)_2$, $SrSiO_3$, $3SrO.Al_2O_3$, $SrSO_4$, $SrB_6$, $SrS$, $SrBr_2$, $SrC_2$, $SrCl_2$, $SrI_2$ and $SrWO_4$. Additionally, beta emitters based on materials other than strontium-90 may also be compatible with this disclosure. Such beta emitters may include Copper-66, Lead-209, Praseodymium-145, Tellurium-127, Tin-121, Nickel-66, Yttrium-90, Bismuth-210, Erbium-169, Praseodymium-143, Phosphorus-32, Phosphorus-33, Strontium-89, Yttrium-91, Tungsten-188, Sulfur-35, Tin-123, Calcium-45, Berkelium-249, Ruthenium-106, Thulium-171, Promethium-147, Krypton-85, Hydrogen-3, Cadmium-113m, Plutonium-241, Strontium-90, Argon-42, Samarium-151, Nickel-63, Silicon-32, Argon-39, Carbon-14, Technetium-99, Selenium-79, Beryllium-10, Cesium-135, Palladium-107, Rhenium-187, Indium-115 and Cadmium-113. In particular, after commercial and technical considerations (e.g., energy level and half-life), the following are of particular interest—Strontium-90/Yttrium-90, Strontium-89, Phosphorus-32, Tin-123 and Yttrium-91.

Figure 3:
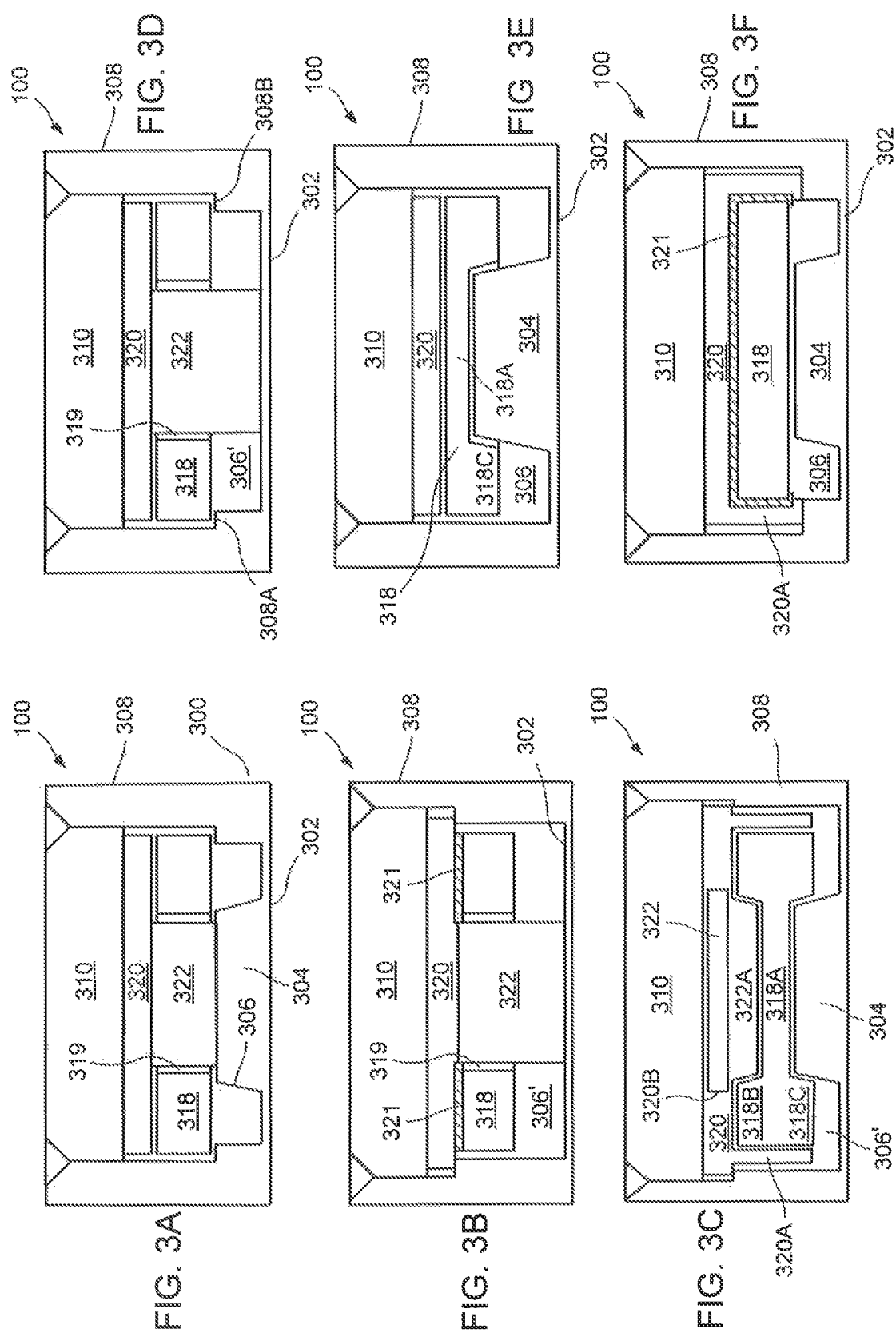
FIGS. 3A-3F illustrates various further embodiments of the radiological source of the present disclosure.

FIGS. 3A through 3F illustrate six further design embodiments of radiological source 100 of the present disclosure. The radiological source 100 of FIG. 3A is very similar to FIG. 1 and includes capsule body 300 includes a lower floor 302, the interior wall of the lower floor 302 including a central plateau 304 on the interior thereof thereby forming a toroidal channel 306 between the central plateau 304 and the outer cylindrical wall 308 of the capsule body 300. The upper edge of outer cylindrical wall 308 forms a circular opening for receiving outer lid 310 which is generally cylindrical. Outer lid 310 is typically welded to capsule body 300, using conventional standards of the industry. Strontium-90 radiological insert 318 is toroidally shaped by rotating a rectangular cross-section about the central axis thereby resulting in a central passageway 319. Toroidally-shaped radiological insert 318 is positioned above the toroidal channel 306, and supported by central plateau 304 and shoulder 308A, 308B formed within an interior of outer cylindrical wall 308. A cylindrical disk-shaped spacer 320, typically made of titanium or stainless steel, is positioned between the radiological insert 318 and the lower surface of the outer lid 310. Additionally, a cylindrical shielding insert 322, typically made from titanium or stainless steel, inserted within the central aperture 319. The shape of the strontium-90 radiological insert 318 leads to increased radiation output around the periphery, with a reduced radiation output within the central aperture 319. This, in combination with the increased shielding in the central area of central plateau 304 and the cylindrical shielding insert 322, results in a flat beam profile, achieving a more constant absorbed dose rate throughout a target volume of tissue of therapeutic interest that is located in front of the source (i.e., anisotropic) characteristic of the resulting beta radiation.

The embodiment of radiological source 100 in FIG. 3B is similar to that of FIG. 3A. The interior wall of lower floor 302 is generally planar without the central plateau of FIG. 3A. The toroidal-shaped strontium-90 radiological insert 318 is secured to cylindrical disk-shaped spacer 320 by a low-melting glass bond 321 or similar configuration. Cylindrical shielding insert 322 extends from spacer 320 to the inner wall of lower floor 302, thereby resulting in a configuration with a toroidal-shaped void 306' below the toroidal-shaped strontium-90 radiological insert 318. The shape of the strontium-90 radiological insert 318 leads to an increased radiation source around the periphery, with a removal of a source of radiation within the central aperture 319. This, in combination with the increased shielding of the cylindrical shielding insert 322, results in a flat beam profile, achieving a more constant absorbed dose rate throughout a target volume of tissue of therapeutic interest that is located in front of the source).

The embodiment of radiological source 100 in FIG. 3C is similar to that of FIG. 3A. The toroidal-shaped strontium-90 radiological insert 318 includes a central cylindrical disk portion 318A and further includes upper and lower toroidal portions 318B, 318C, respectively, extending around the circumference thereof. Additionally, spacer 320 further includes a downwardly extending cylindrical skirt 320A which outwardly abuts the circumference of toroidal-shaped strontium-90 radiological insert 318. Spacer 320 further includes a central cylindrical aperture 320B which receives a variation of shielding insert 322, further including a downwardly extending frusto-conical portion 322A for engaging against central cylindrical disk portion 318A of strontium-90 radiological insert 318 and being positioned within the upper toroidal portion 318B of strontium-90 radiological insert 318. This configuration engages the central cylindrical disk portion 318A between the downwardly extending frusto-conical portion 322A of shielding insert 322 and central plateau 304. Similar to the embodiment of FIG. 3B, a toroidal-shaped void 306' is formed between the lower toroidal portion 318C of strontium-90 radiological insert 318 and the inner wall of floor 302. The shape of the strontium-90 radiological insert 318 leads to an increased radiation source around the periphery, with a reduction in the radiation from cylindrical disk portion 318A. This, in combination with the increased shielding of the central plateau 304, results in a flat beam profile, achieving a more constant absorbed dose rate throughout a target volume of tissue of therapeutic interest that is located in front of the source).

The embodiment of FIG. 3D is similar to that of FIG. 3B. However, the interior of cylindrical wall 308 includes shoulders 308A, 308B for supporting the toroidal-shaped strontium-90 radiological insert 318 above the toroidal channel 306. This may eliminate the need for the low melting glass bond 321 or similar configuration to affix the toroidal-shaped strontium-90 radiological insert 318 to the spacer 320. The shape of the strontium-90 radiological insert 318 leads to an increased radiation source around the periphery, with a removal of a source of radiation within the central aperture 319. This, in combination with the increased shielding of the cylindrical shielding insert 322, results in a flat beam profile, achieving a more constant absorbed dose rate throughout a target volume of tissue of therapeutic interest that is located in front of the source).

The embodiment of FIG. 3E is similar to that of FIG. 3C. The toroidal-shaped strontium-90 radiological insert 318 includes a central cylindrical disk portion 318A and further includes a lower toroidal portion 318C extending around the circumference thereof. The lack of a upper toroidal portion allows the spacer 320 to be simplified to a cylindrical disk shape. The shape of the strontium-90 radiological insert 318 leads to an increased radiation source around the periphery, with a reduction in the radiation from cylindrical disk portion 318A. This, in combination with the increased shielding of the central plateau 304, results in a flat beam profile, achieving a more constant absorbed dose rate throughout a target volume of tissue of therapeutic interest that is located in front of the source).

The embodiment of FIG. 3F is similar to that of FIG. 3E. The strontium-90 radiological insert 318 is simplified to a disk shape, rather than a toroidal shape. Additionally, spacer 320 further includes a downwardly extending cylindrical skirt 320A which outwardly abuts the circumference of toroidal-shaped strontium-90 radiological insert 318. The strontium-90 radiological insert 318 is secured to cylindrical disk-shaped spacer 320 by a low-melting glass bond 321 so as to be suspended above central plateau 304 and toroidal channel 306. It is envisioned that this embodiment could further have the strontium-90 radiological insert 318 contacting and being supported, at least in part, by central plateau 304.

Figure 6:
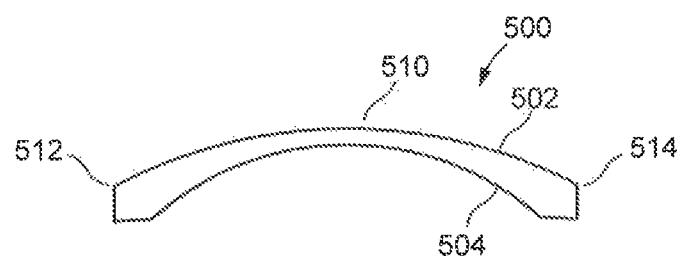
FIG. 6 illustrates a still further embodiment of the radiological source of the present disclosure, including a minus-lens meniscus shape.

The embodiment of FIG. 6 is a Strontium-90 radiological insert 500 with a (rotationally symmetric) minus-lens meniscus shape wherein there are two different curvatures on the upper and lower surfaces 502, 504. The upper surface 502 (or "rear") is convex, the lower surface 504 (or "face") is concave 504 and the radiological insert 500 is thinner at its center 510 (i.e., along the rotational axis) than at its edges 512, 514. Typically, this minus-lens meniscus shape may be implemented by having a shorter radius of curvature for the lower surface 504 than for the upper surface 502. While not shown, this radiological insert 500 will typically be encased by an encapsulation or capsule body 300 similar to that shown in FIGS. 3A-3F, possibly with increased shielding in a central portion thereof (that is, below the center 510) in order to achieve a flatter radiation profile. This meniscus configuration may be considered, from a mathematical point of view, to be mid-way between a cylindrical or flat disk and a toroidal "donut-shaped" configuration. The configuration may be termed "meniscus," "biconcave," or "planar concave."

Figures 7A, 7B:
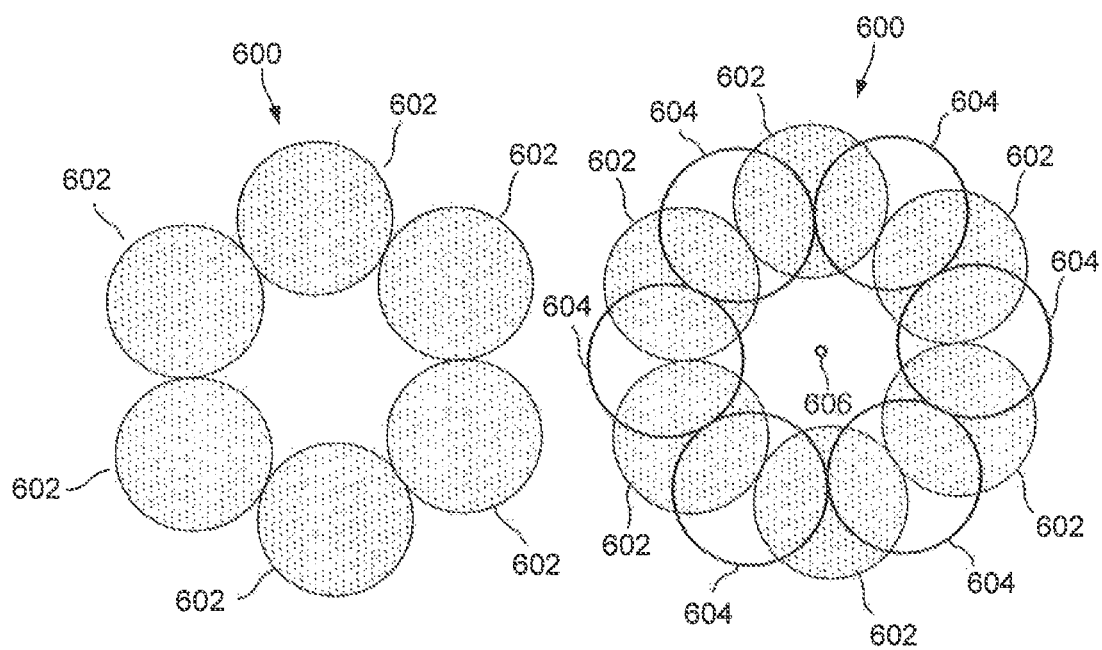
FIGS. 7A and 7B illustrate a still further embodiment of the radiological source of the present disclosure, wherein multiple elements are placed in a quasi-toroidal shape in one or two layers.

The embodiment of FIG. 7A illustrates a Strontium-90 radiological insert 600 comprising a ring of disk-like sub-elements of Strontium-90 602 arranged in a quasi-toroidal shape. Similarly, the embodiment of FIG. 7B illustrates a Strontium-90 radiological insert 600 comprising a first ring of disk-like sub-elements of Strontium-90 602 arranged in a quasi-toroidal shape, with second ring of disk-like sub-elements of Strontium-90 604, rotationally offset by the radius or one half of the expanse of one disk from the first ring, and axially offset, typically by the thickness of the sub-elements 602, 604. The first and second rings are adjacent to each other and share a common rotational axis 606. The embodiments of FIGS. 7A and 7B further include a sealed encapsulation.

Figure 8A:
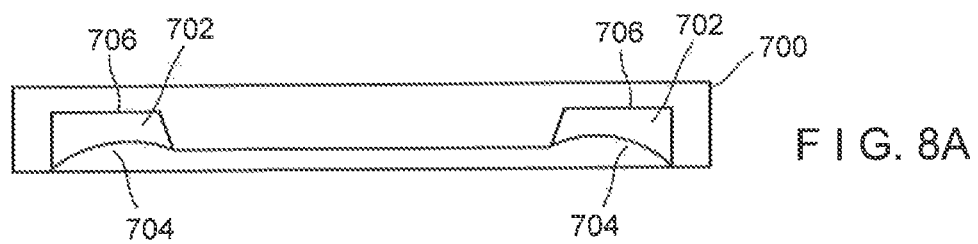
FIGS. 8A, 8B and 8C illustrate yet still further embodiments of the radiological source of the present disclosure.
Figure 8B:
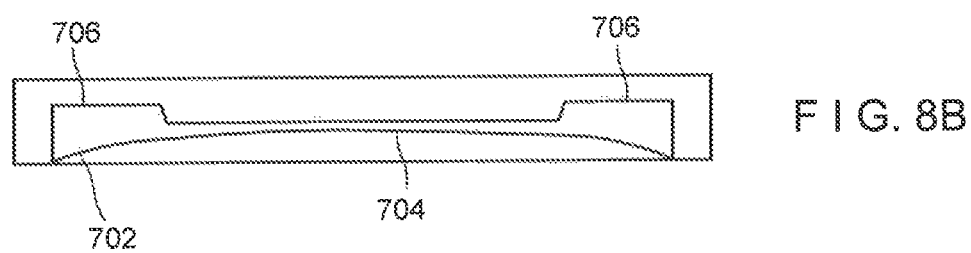
Figure 8C:
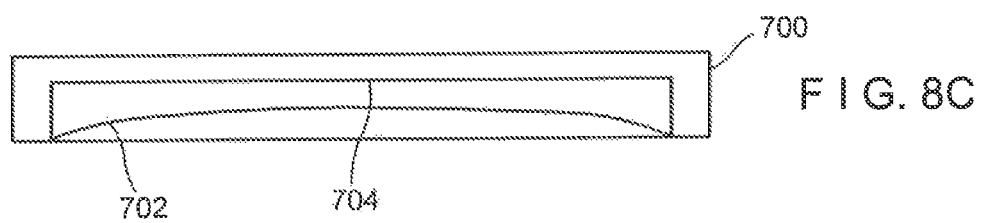

The embodiments of FIGS. 8A, 8B and 8C include a metallic, ceramic or similar dish 700 into which fused Sr-90 glass 702 is melted and bonded. The Sr-90 glass 702, in a viscous state, is poured into the dish in an inverted position from that shown in FIGS. 8A, 8B and 8C so as to form a meniscus 704 (the illustrated concave surface). In order to increase the amount of Sr-90 glass at the peripheral portions of the dish 700, toroidal troughs 706 may be formed such as is illustrated in FIGS. 8A and 8B. These embodiments of FIGS. 8A, 8B and 8C further include a sealed encapsulation.

Further alternatives to the present disclosure include fixation of the active insert using glass, such as glass pre-melted into a stainless steel insert, glass powder co-compacted with a ceramic and glass powder mixed with a ceramic and then compacted. Additionally, alternatives include fixation of the active insert using mechanical methods such as soft materials such as copper, silver, aluminum, etc. or the use of springs of various types (wave, conical, folded disk, etc.). Further alternatives include active insert centering features to prevent positional errors such as tapered ceramic disks or a disk with an aperture or protrusion which interfaces with the capsule lid.

Similarly, the various embodiments of the radiological sources which include a cavity could be implemented by filling the cavity with radioactive microspheres. Such shapes would be defined by the shape of the cavity inside the source, while the microspheres could be immobilized using washers, spaces or similar devices during assembly. Further alternative embodiments include radioactive microspheres which are bonded using a fused glass/enamel bonding material to an insert (e.g., a metal or ceramic support) to immobilize the microspheres and define their shape.

In a further aspect of this disclosure, aqueous ammonia solution ($NH_4OH$) is added to a mixed aqueous solution containing dissolved radioactive strontium nitrate $^{90}Sr(NO_3)_2$ and dissolved silver nitrate ($AgNO_3$) (gold or copper may be substituted for silver in some applications, mixtures of silver, gold or copper may also be used) and a mixed precipitate can form of sparingly soluble silver hydroxide AgOH (some of which may convert to silver oxide $Ag_2O$ plus water in situ) and strontium hydroxide $^{90}Sr(OH)_2$. Soluble ammonium nitrate $NH_4NO_3$ remains in solution. Excess ammonium hydroxide produces a water-soluble ammoniacal silver complex $[Ag(NH_3)_2OH]$ while the strontium hydroxide remains insoluble. The solution and/or the mixed precipitates can be evaporated so that all solids co-precipitate or crystalize out of solution to produce an intimate mixture. These solids are baked dry so that the ammonium nitrate decomposes and sublimes (above 250° Centigrade) leaving substantially nothing behind, silver hydroxide decomposes to silver oxide then further decomposes to silver metal and the strontium hydroxide decomposes to strontium oxide. What is left is an intimate mixture of silver metal and strontium oxide ($^{90}SrO+Ag$). Because silver is a soft semi-precious metal, such an intimate mixture of silver and radioactive strontium oxide can be mechanically and/or thermally formed into thin toroidal insert shapes by processes such as pressing, forging, rolling, extrusion and/or sintering.

Silver hydroxide or silver oxide can be prepared and pressed into a disk shape (toroidal or flat) at a pressure sufficient to bind the particles together to produce a handleable green-state disk (an organic or inorganic binder can be added if needed) but at a pressure that is low enough to leave porosity or microporosity within the disk. Aqueous strontium nitrate $^{90}Sr(NO_3)_2$ can then be soaked into the disk and then dried down to achieve intimate mixing. The dried disk can be sintered to produce a fully dense cermet containing strontium oxide embedded or immobilized within the matrix formed of copper oxide, silver oxide, copper hydroxide, silver hydroxide, gold hydroxide (i.e., auric acid) or mixtures thereof. The proportions of strontium and silver (or gold, copper or mixtures thereof) can be varied, resulting in different mechanical properties. Less strontium produces more ductility but a thicker more-attenuating disk. The typical range of composition can be 2-50 mol percent of strontium oxide in silver, gold or copper, preferably 5-40 mol percent, more preferably 10-30 mol percent. Cermet disks can be re-pressed or otherwise mechanically or thermally treated after sintering to further densify or remold the shape of the disks.

In a further aspect of this disclosure, Strontium-90 compounds are incorporated or mixed with aluminum to make a composite material. This may be performed by a method of incorporating Strontium-90 into aluminum by mixing or blending strontium fluoride ($^{90}SrF_2$) powder with aluminum powder, compressing the mixture into a billet, then heating it to about 10° Centigrade below the melting point of aluminum (660.3° Centigrade) before extruding the billet through an aperture in a metal collar to produce a wire of $^{90}SrF_2+Al$. The resulting material can be formed into a toroidal disk or similar configuration as described in this disclosure.

Strontium fluoride is a stable material. It melts at 1477° Centigrade and is insoluble in water ($K_{sp}$ value is approximately $2.0 \times 10^{-10}$ at 25° Centigrade). It can be made from commercially available strontium nitrate $^{90}Sr(NO_3)_2$ by adding soluble ammonium fluoride to a strontium nitrate solution, precipitating insoluble strontium fluoride ($^{90}SrF_2$) and mixing/blending the dried salt with aluminum powder before pressing the mixture/blend into a disk. Useful ratios of $^{90}SrF_2$ to Al could typically be in the range 5-50% of $^{90}SrF_2$, preferably 10-30% (by weight). The resulting material can be formed into a toroidal disk or similar configuration as described in this disclosure.

Alternatively, an aqueous solution of $^{90}Sr(NO_3)_2$ could be absorbed into a disk made of porous or microporous aluminum and then dried down and baked above the decomposition temperature of $^{90}Sr(NO_3)_2$ of 570° Centigrade but below the melting point of aluminum 660.3° Centigrade in a non-oxidizing atmosphere, to convert the strontium nitrate into strontium oxide. This could be achieved in a vacuum oven or under an inert gas such as argon or a reducing atmosphere such as an argon-hydrogen mixture. Other soluble forms of Strontium-90 could be absorbed and baked in similar ways. The resulting material can be formed into a toroidal disk or similar configuration as described in this disclosure.

Thus the several aforementioned objects and advantages are most effectively attained. Although preferred embodiments of the invention have been disclosed and described in detail herein, it should be understood that this invention is in no sense limited thereby.

What is claimed is:

1. A radiological insert with an upper convex surface and a lower concave surface, wherein a radius of curvature of the lower concave surface is shorter than a radius of curvature of the upper convex surface;
   wherein the radiological insert is rotationally symmetric with a minus-lens meniscus shape;
   wherein a center of the radiological insert is thinner than edges of the radiological insert; and
   wherein the radiological insert is a beta-emitter.

2. The radiological insert of claim 1 wherein the radiological insert includes strontium-90, wherein the strontium-90 is contained in a material or compound selected from the group consisting of a strontium ceramic, a strontium glass, $SrF_2$, $Sr_2P_2O_7$, $SrTiO_3$, SrO, $Sr_2TiO_4$, $SrZrO_3$, $SrCO_3$, $Sr(NbO_3)_2$, $SrSiO_3$, $3SrO.Al_2O_3$, $SrSO_4$, $SrB_6$, SrS, $SrBr2$, $SrC_2$, $SrCl_2$, $SrI_2$ and $SrWO_4$.

3. The radiological insert of claim 1 wherein the radiological insert includes a beta source, contained in a material or compound, wherein the beta source is selected from the group consisting of Copper-66, Lead-209, Praseodymium-145, Tellurium-127, Tin-121, Nickel-66, Yttrium-90, Bismuth-210, Erbium-169, Praseodymium-143, Phosphorus-32, Phosphorus-33, Strontium-89, Yttrium-91, Tungsten-188, Sulfur-35, Tin-123, Calcium-45, Berkelium-249, Ruthenium-106, Thulium-171, Promethium-147, Krypton-85, Hydrogen-3, Cadmium-113m, Plutonium-241, Strontium-90, Argon-42, Samarium-151, Nickel-63, Silicon-32, Argon-39, Carbon-14, Technetium-99, Selenium-79, Beryllium-10, Cesium-135, Palladium-107, Rhenium-187, Indium-115 and Cadmium-113.

\* \* \* \* \*